US009770330B2

(12) United States Patent
Maurer et al.

(10) Patent No.: US 9,770,330 B2
(45) Date of Patent: *Sep. 26, 2017

(54) IMPLANT DELIVERY SYSTEM AND METHOD

(71) Applicant: Cardiosolutions, Inc., West Bridgewater, MA (US)

(72) Inventors: Christopher William Maurer, Wakefield, MA (US); Jonathan Edward Wilson, Amesbury, MA (US)

(73) Assignee: Cardiosolutions, Inc., West Bridgewater, MA (US)

( * ) Notice: Subject to any disclaimer, the term of this patent is extended or adjusted under 35 U.S.C. 154(b) by 172 days.

This patent is subject to a terminal disclaimer.

(21) Appl. No.: 14/484,611

(22) Filed: Sep. 12, 2014

(65) Prior Publication Data

US 2014/0379075 A1 Dec. 25, 2014

Related U.S. Application Data

(62) Division of application No. 11/940,694, filed on Nov. 15, 2007, now Pat. No. 8,852,270.

(51) Int. Cl.
*A61F 2/24* (2006.01)

(52) U.S. Cl.
CPC .......... *A61F 2/2442* (2013.01); *A61F 2/2466* (2013.01); *A61F 2/246* (2013.01)

(58) Field of Classification Search
CPC ........ A61F 2/24; A61F 2/2418; A61F 2/2412; A61F 2/01; A61F 2/2442
See application file for complete search history.

(56) References Cited

U.S. PATENT DOCUMENTS 2,625,967 A   1/1953   Stull
2,549,731 A   4/1954   Wattley
(Continued)

FOREIGN PATENT DOCUMENTS

CN    1961983 A     5/2007
CN    101484093 A   7/2009
(Continued)

OTHER PUBLICATIONS

Acar, et al., "AREVA: Multicenter Randomized Comparison of Low-Dose Versus Standard-Dose Anticoagulation in Patients With Mechanical Prosthetic Heart Valves," Circulation, Nov. 1, 1996, pp. 2107-2112, vol. 94, No. 9.
(Continued)

*Primary Examiner* — Jason-Dennis Stewart
(74) *Attorney, Agent, or Firm* — Thomas J. Engellenner; Reza Mollaaghababa; Pepper Hamilton LLP

(57) ABSTRACT

An implant delivery system may comprise a catheter including at least one lumen, a guide wire configured to be received in the lumen, and an implant. The guide wire may comprise a clamping mechanism disposed about a distal end of the guide wire. The clamping mechanism may include a first and at least a second jaw wherein at least one of the jaws is configured to pivot between a closed position wherein the jaws define at least one internal cavity between the jaws configured to receive at least a portion of the implant and an open position configured to release the implant. The implant may be configured to be received in the lumen and may comprise a driver configured to be releasably received in the cavity of the clamping mechanism.

18 Claims, 8 Drawing Sheets

(56) References Cited

U.S. PATENT DOCUMENTS

| | | |
|---|---|---|
| 3,197,788 A | 8/1965 | Segger |
| 3,445,916 A | 5/1969 | Schulte |
| 3,551,913 A | 1/1971 | Shiley et al. |
| 3,586,029 A | 6/1971 | Evers et al. |
| 3,589,392 A | 6/1971 | Meyer |
| 3,671,979 A | 6/1972 | Moulopoulos |
| 3,689,942 A | 9/1972 | Rapp |
| 3,714,671 A | 2/1973 | Edwards et al. |
| 3,739,402 A | 6/1973 | Cooley et al. |
| 3,983,581 A | 10/1976 | Angell et al. |
| 4,079,468 A | 3/1978 | Liotta et al. |
| 4,084,268 A | 4/1978 | Lonescu et al. |
| 4,246,893 A | 1/1981 | Berson |
| 4,259,753 A | 4/1981 | Liotta et al. |
| 4,291,420 A | 9/1981 | Reul |
| 4,297,749 A | 11/1981 | Davis et al. |
| 4,439,185 A | 3/1984 | Lundquist |
| 4,535,757 A | 8/1985 | Webster, Jr. |
| 4,597,767 A | 7/1986 | Lenkei |
| 4,836,204 A | 6/1989 | Landymore et al. |
| 4,865,030 A | 9/1989 | Polyak |
| 4,960,424 A | 10/1990 | Grooters |
| 5,002,067 A | 3/1991 | Berthelsen et al. |
| 5,217,484 A | 6/1993 | Marks |
| 5,222,973 A | 6/1993 | Sharpe et al. |
| 5,261,916 A | 11/1993 | Engelson |
| 5,304,195 A | 4/1994 | Twyford, Jr. et al. |
| 5,308,357 A | 5/1994 | Lichtman |
| 5,318,589 A | 6/1994 | Lichtman |
| 5,350,397 A | 9/1994 | Palermo et al. |
| 5,397,351 A | 3/1995 | Pavcnik et al. |
| 5,411,552 A | 5/1995 | Andersen et al. |
| 5,415,667 A | 5/1995 | Frater |
| 5,462,527 A | 10/1995 | Stevens-Wright et al. |
| 5,509,428 A | 4/1996 | Dunlop |
| 5,554,185 A | 9/1996 | Block et al. |
| 5,582,607 A | 12/1996 | Lackman |
| 5,611,800 A | 3/1997 | Davis et al. |
| 5,634,936 A | 6/1997 | Linden et al. |
| 5,638,827 A | 6/1997 | Palmer et al. |
| 5,649,949 A | 7/1997 | Wallace et al. |
| 5,653,712 A | 8/1997 | Stern |
| 5,665,100 A | 9/1997 | Yoon |
| 5,713,954 A | 2/1998 | Rosenberg et al. |
| 5,776,075 A | 7/1998 | Palmer |
| 5,792,179 A | 8/1998 | Sideris |
| 5,797,958 A | 8/1998 | Yoon |
| 5,814,098 A | 9/1998 | Hinnenkamp et al. |
| 5,840,081 A | 11/1998 | Andersen et al. |
| 5,891,130 A | 4/1999 | Palermo et al. |
| 5,895,391 A | 4/1999 | Farnholtz |
| 5,928,224 A | 7/1999 | Laufer |
| 5,957,865 A | 9/1999 | Backman et al. |
| 5,957,949 A | 9/1999 | Leonhardt et al. |
| 5,964,806 A | 10/1999 | Cook et al. |
| 5,989,242 A | 11/1999 | Saadat et al. |
| 5,993,474 A | 11/1999 | Ouchi |
| 6,090,096 A | 7/2000 | St. Goar et al. |
| 6,152,144 A | 11/2000 | Lesh et al. |
| 6,168,614 B1 | 1/2001 | Andersen et al. |
| 6,183,512 B1 | 2/2001 | Howanec et al. |
| 6,190,373 B1 | 2/2001 | Palermo et al. |
| 6,217,610 B1 | 4/2001 | Carpentier et al. |
| 6,283,127 B1 | 9/2001 | Sterman et al. |
| 6,283,995 B1 | 9/2001 | Moe et al. |
| 6,287,339 B1 | 9/2001 | Vazquez et al. |
| 6,332,893 B1 | 12/2001 | Mortier et al. |
| 6,358,277 B1 | 3/2002 | Duran |
| 6,406,420 B1 | 6/2002 | McCarthy et al. |
| 6,415,693 B1 | 7/2002 | Simon et al. |
| 6,416,549 B1 | 7/2002 | Chinn et al. |
| 6,419,695 B1 | 7/2002 | Gabbay |
| 6,440,132 B1 | 8/2002 | Jackson |
| 6,454,798 B1 | 9/2002 | Moe |
| 6,461,382 B1 | 10/2002 | Cao |
| 6,482,228 B1 | 11/2002 | Norred |
| 6,508,825 B1 | 1/2003 | Selmon et al. |
| 6,592,606 B2 | 7/2003 | Huter et al. |
| 6,629,534 B1 | 10/2003 | St. Goar et al. |
| 6,652,578 B2 | 11/2003 | Bailey et al. |
| 6,673,100 B2 | 1/2004 | Diaz et al. |
| 6,682,559 B2 | 1/2004 | Myers et al. |
| 6,695,866 B1 | 2/2004 | Kuehn et al. |
| 6,746,404 B2 | 6/2004 | Schwartz |
| 6,764,510 B2 | 7/2004 | Vidlund et al. |
| 6,767,362 B2 | 7/2004 | Schreck |
| 6,769,434 B2 | 8/2004 | Liddicoat et al. |
| 6,805,711 B2 | 10/2004 | Quijano et al. |
| 6,821,297 B2 | 11/2004 | Snyders |
| 6,830,584 B1 | 12/2004 | Seguin |
| 6,830,585 B1 | 12/2004 | Artoff et al. |
| 6,849,081 B2 | 2/2005 | Sepetka et al. |
| 6,869,444 B2 | 3/2005 | Gabbay |
| 6,896,700 B2 | 5/2005 | Lu et al. |
| 6,911,043 B2 | 6/2005 | Myers et al. |
| 6,964,684 B2 | 11/2005 | Ortiz et al. |
| 6,971,998 B2 | 12/2005 | Rosenman et al. |
| 6,974,476 B2 | 12/2005 | McGuckin, Jr. et al. |
| 6,976,950 B2 | 12/2005 | Connors et al. |
| 6,978,176 B2 | 12/2005 | Lattouf |
| 6,997,951 B2 | 2/2006 | Solem et al. |
| 7,018,406 B2 | 3/2006 | Seguin et al. |
| 7,056,286 B2 | 6/2006 | Ravenscroft et al. |
| 7,070,618 B2 | 7/2006 | Streeter |
| 7,077,862 B2 | 7/2006 | Vidlund et al. |
| 7,101,395 B2 | 9/2006 | Tremulis et al. |
| 7,112,219 B2 | 9/2006 | Vidlund et al. |
| 7,160,322 B2 | 1/2007 | Gabbay |
| 7,189,199 B2 | 3/2007 | McCarthy et al. |
| 7,247,134 B2 | 7/2007 | Vidlund et al. |
| 7,335,213 B1 | 2/2008 | Hyde et al. |
| 7,344,553 B2 | 3/2008 | Opolski et al. |
| 7,374,572 B2 | 5/2008 | Gabbay |
| 7,381,210 B2 | 6/2008 | Zarbatany et al. |
| 7,404,824 B1 | 7/2008 | Webler et al. |
| 7,657,326 B2 | 2/2010 | Bodner et al. |
| 7,678,145 B2 | 3/2010 | Vidlund et al. |
| 7,704,268 B2 | 4/2010 | Chanduszko |
| 7,753,949 B2 | 7/2010 | Lamphere et al. |
| 7,785,366 B2 | 8/2010 | Maurer et al. |
| 7,927,370 B2 | 4/2011 | Webler et al. |
| 7,942,928 B2 | 5/2011 | Webler et al. |
| 7,963,973 B2 | 6/2011 | Nguyen et al. |
| 8,092,525 B2 | 1/2012 | Eliasen et al. |
| 8,118,822 B2 | 2/2012 | Schaller et al. |
| 8,216,302 B2 | 7/2012 | Wilson et al. |
| 8,486,136 B2 | 7/2013 | Maurer et al. |
| 8,506,623 B2 | 8/2013 | Wilson et al. |
| 2001/0007956 A1 | 7/2001 | Letac et al. |
| 2001/0010017 A1 | 7/2001 | Cribier et al. |
| 2001/0018611 A1 | 8/2001 | Solem et al. |
| 2002/0029080 A1 | 3/2002 | Mortier et al. |
| 2002/0032480 A1 | 3/2002 | Spence et al. |
| 2002/0042651 A1 | 4/2002 | Liddicoat et al. |
| 2002/0058995 A1 | 5/2002 | Stevens |
| 2002/0077566 A1 | 6/2002 | Laroya et al. |
| 2002/0081553 A1 | 6/2002 | Tramonte |
| 2002/0169377 A1 | 11/2002 | Khairkhahan et al. |
| 2002/0169502 A1 | 11/2002 | Mathis |
| 2002/0183838 A1 | 12/2002 | Liddicoat et al. |
| 2002/0188170 A1 | 12/2002 | Santamore et al. |
| 2003/0033009 A1 | 2/2003 | Gabbay |
| 2003/0040792 A1 | 2/2003 | Gabbay |
| 2003/0105519 A1 | 6/2003 | Fasol et al. |
| 2003/0120264 A1 | 6/2003 | Lattouf |
| 2003/0130731 A1 | 7/2003 | Vidlund et al. |
| 2003/0139751 A1 | 7/2003 | Evans et al. |
| 2003/0144574 A1 | 7/2003 | Heilman et al. |
| 2003/0181945 A1 | 9/2003 | Opalski et al. |
| 2003/0199975 A1 | 10/2003 | Gabbay |
| 2003/0208203 A1 | 11/2003 | Lim et al. |
| 2003/0212453 A1 | 11/2003 | Mathis et al. |
| 2004/0034366 A1 | 2/2004 | van der Burg et al. |
| 2004/0044402 A1 | 3/2004 | Jung et al. |

(56) References Cited

U.S. PATENT DOCUMENTS

| | | |
|---|---|---|
| 2004/0088047 A1 | 5/2004 | Spence et al. |
| 2004/0106989 A1 | 6/2004 | Wilson et al. |
| 2004/0122512 A1 | 6/2004 | Navia et al. |
| 2004/0127981 A1 | 7/2004 | Rahdert et al. |
| 2004/0127983 A1 | 7/2004 | Mortier et al. |
| 2004/0148019 A1 | 7/2004 | Vidlund et al. |
| 2004/0148020 A1 | 7/2004 | Vidlund et al. |
| 2004/0181256 A1 | 9/2004 | Glaser |
| 2004/0210304 A1 | 10/2004 | Seguin et al. |
| 2004/0210307 A1 | 10/2004 | Khairkhahan |
| 2004/0225353 A1 | 11/2004 | McGuckin, Jr. et al. |
| 2004/0225354 A1 | 11/2004 | Allen et al. |
| 2004/0243229 A1 | 12/2004 | Vidlund et al. |
| 2004/0260322 A1 | 12/2004 | Rudko et al. |
| 2005/0021056 A1 | 1/2005 | St. Goar et al. |
| 2005/0027337 A1 | 2/2005 | Rudko et al. |
| 2005/0033446 A1 | 2/2005 | Deem et al. |
| 2005/0038508 A1 | 2/2005 | Gabbay |
| 2005/0038509 A1 | 2/2005 | Ashe |
| 2005/0065591 A1 | 3/2005 | Moberg et al. |
| 2005/0070999 A1 | 3/2005 | Spence |
| 2005/0075727 A1 | 4/2005 | Wheatley |
| 2005/0090824 A1 | 4/2005 | Shluzas et al. |
| 2005/0131451 A1 | 6/2005 | Kleshinski et al. |
| 2005/0149182 A1 | 7/2005 | Alferness et al. |
| 2005/0159810 A1 | 7/2005 | Filsoufi |
| 2005/0222488 A1 | 10/2005 | Chang et al. |
| 2005/0229433 A1 | 10/2005 | Cachia |
| 2005/0288786 A1 | 12/2005 | Chanduszko |
| 2006/0020335 A1 | 1/2006 | Kowalsky et al. |
| 2006/0025855 A1 | 2/2006 | Lashinski et al. |
| 2006/0058871 A1 | 3/2006 | Zakay et al. |
| 2006/0084943 A1 | 4/2006 | Rosenman et al. |
| 2006/0129025 A1 | 6/2006 | Levine et al. |
| 2006/0149368 A1 | 7/2006 | Spence |
| 2006/0155326 A1 | 7/2006 | Aranyi |
| 2006/0178700 A1 | 8/2006 | Quinn |
| 2006/0195012 A1 | 8/2006 | Mortier et al. |
| 2006/0195185 A1 | 8/2006 | Lane et al. |
| 2006/0199995 A1 | 9/2006 | Vijay |
| 2006/0229708 A1 | 10/2006 | Powell et al. |
| 2006/0241745 A1 | 10/2006 | Solem |
| 2006/0253072 A1 | 11/2006 | Pai et al. |
| 2006/0293698 A1 | 12/2006 | Douk |
| 2007/0016286 A1 | 1/2007 | Herrmann et al. |
| 2007/0049980 A1 | 3/2007 | Zielinski et al. |
| 2007/0093890 A1 | 4/2007 | Eliasen et al. |
| 2007/0118151 A1 | 5/2007 | Davidson |
| 2007/0167981 A1 | 7/2007 | Opalski et al. |
| 2007/0185571 A1 | 8/2007 | Kapadia et al. |
| 2007/0198050 A1 | 8/2007 | Ravenscroft et al. |
| 2007/0198082 A1 | 8/2007 | Kapadia et al. |
| 2007/0213578 A1 | 9/2007 | Khairkhahan et al. |
| 2007/0232981 A1 | 10/2007 | Ravenscroft et al. |
| 2007/0232992 A1 | 10/2007 | Kutsko et al. |
| 2007/0239154 A1 | 10/2007 | Shaolian et al. |
| 2007/0255399 A1 | 11/2007 | Eliasen et al. |
| 2007/0265700 A1 | 11/2007 | Eliasen et al. |
| 2007/0282429 A1 | 12/2007 | Hauser et al. |
| 2007/0293943 A1 | 12/2007 | Quinn |
| 2008/0125860 A1 | 5/2008 | Webler et al. |
| 2008/0125861 A1 | 5/2008 | Webler et al. |
| 2008/0183105 A1 | 7/2008 | Greenhalgh et al. |
| 2008/0195200 A1 | 8/2008 | Vidlund et al. |
| 2008/0208329 A1 | 8/2008 | Bishop et al. |
| 2008/0288061 A1 | 11/2008 | Maurer et al. |
| 2009/0043382 A1 | 2/2009 | Maurer et al. |
| 2009/0048668 A1 | 2/2009 | Wilson et al. |
| 2009/0082874 A1 | 3/2009 | Cachia |
| 2009/0093670 A1 | 4/2009 | Annest et al. |
| 2009/0105814 A1 | 4/2009 | Groothuis et al. |
| 2009/0131849 A1 | 5/2009 | Maurer et al. |
| 2009/0131880 A1 | 5/2009 | Speziali et al. |
| 2009/0132033 A1 | 5/2009 | Maurer et al. |
| 2009/0163934 A1 | 6/2009 | Raschdorf, Jr. et al. |
| 2009/0240326 A1 | 9/2009 | Wilson et al. |
| 2010/0016655 A1 | 1/2010 | Annest et al. |
| 2010/0022948 A1 | 1/2010 | Wilson et al. |
| 2010/0324668 A1 | 12/2010 | Maurer et al. |
| 2012/0143320 A1 | 6/2012 | Eliasen et al. |
| 2013/0211513 A1 | 8/2013 | Rourke et al. |
| 2015/0127097 A1 | 5/2015 | Neumann et al. |

FOREIGN PATENT DOCUMENTS

| | | |
|---|---|---|
| EP | 1323438 | 2/2003 |
| EP | 0125393 | 8/2007 |
| GB | 1264472 | 2/1972 |
| GB | 1268484 | 3/1972 |
| GB | 1388064 | 3/1975 |
| WO | 8900030 A1 | 1/1989 |
| WO | WO 03049619 | 6/2003 |
| WO | WO 2006032051 | 3/2006 |
| WO | WO 2006064490 | 6/2006 |
| WO | WO 2006091597 | 8/2006 |
| WO | WO 2006111391 | 10/2006 |
| WO | WO 2006127509 | 11/2006 |
| WO | WO 2007064810 | 6/2007 |
| WO | WO 2007078772 | 7/2007 |
| WO | WO 2007100409 | 9/2007 |
| WO | WO 2007140470 | 12/2007 |
| WO | WO 2008079828 | 7/2008 |
| WO | 2008141322 A1 | 11/2008 |
| WO | WO 2009053952 | 4/2009 |

OTHER PUBLICATIONS

Acker, et al., "Mitral valve surgery in heart failure: Insights from the Acorn Clinical Trial, Surgery for Acquired Cardiovascular Disease," The Journal of Thoracic and Cardiovascular Surgery, Sep. 2006, pp. 568-577.e4, vol. 132, No. 3.

A first for MiCardia's Dynoplasty, Medical Device Daily, Feb. 19, 2009, vol. 13, No. 32, 1 page.

Babaliaros, et al., "Emerging Applications for Transseptal Left Heart Catheterization-Old Techniques for New Procedures," Journal of the American College of Cardiology, Jun. 3, 2008, pp. 2116-2122, vol. 51, No. 22.

Bailey, et al., "The Surgical Correction of Mitral Insufficiency by the Use of Pericardia! Grafts" Dec. 1954 (pp. 551-627).

Bailey, et al., "Surgical Repair of Mitral Insufficiency," Feb. 1951 (pp. 125-182).

Bailey, et al., "Closed Intracardiac Tactile Surgery," Jul. 1952 (pp. 1-24).

Balzer, et al. "Real-time transesophageal three-dimensional echocardiography for guidance of percutaneous cardiac interventions: first experience," Clinical Research in Cardiology, May 29, 2008, pp. 565-574, vol. 97, No. 9.

Benichoux, et al., "A Method of Surgical Correction of Mitral Insufficiency," 1955 (pp. 148-158).

Blalock, "A Consideration of Some of the Problems in Cardiovascular Surgery," Jun. 1951 (pp. 543-571).

B-Lundqvist, et al. "Transseptal Left Heart Catheterization: A Review of 278 Studies," Clinical Cardiology Publishing Co., Inc., Jan. 1986, pp. 21-26, vol. 9.

Bonow, et al., "ACC/AHA 2006 Guidelines for the Management of Patients With Valvular Heart Disease: Executive Summary, Circulation-Journal of the American Heart Association," Downloaded from circ.ahajournals.org, Jul. 31, 2008, pp. 449-527.

Borrie, "Mitral Insufficiency: Experimental Circular Suture Around the Atrioventricular Ring," 1955 (pp. 687-697).

Braunberger, et al., "Very Long-Term Results (More Than 20 Years) of Valve Repair With Carpentier's Techniques in Nonrheumatic Mitral Valve Insufficiency," Downloaded from circ.ahajournals.org, Aug. 26, 2008, 1-8-1-11.

Bryan, et al., "Prospective randomized comparison of Carbo Medics and St. Jude Medical bileaflet mechanical heart valve prostheses: Ten-year follow-up," The Journal of Thoracic and Cardiovascular Surgery, Mar. 2007, pp. 614-622.e2, vol. 133, No. 3.

(56) References Cited

OTHER PUBLICATIONS

Burkhoff, MD., Ph.D, et al., "A randomized multicenter clinical study to evaluate the safety and efficacy of the TandemHeart percutaneous ventricular assist device versus conventional therapy with intraaortic balloon pumping for treatment of cardiogenic shock," The Cardiovascular Research Foundation, accepted May 2, 2006, 8 pages.

Byrne, et al., "Percutaneous Mitral Annular Reduction Provides Continued Benefit in an Ovine Model of Dilated Cardiomyopathy," Downloaded from circ.ahajournals.org, Aug. 26, 2008, pp. 3088-3092.

Canadian Office Action dated Sep. 12, issued in Canadian Patent Application No. 2,627,517, 2 pages.

Carlson, et al., "Lead Perforation: Incidence in Registries, Pace Industry Viewpoint," Jan. 2008, pp. 13-15, vol. 31.

Carpentier, et al., "Reconstructive surgery of mitral valve incompetence Ten-year appraisal," The Journal of Thoracic and Cardiovascular Surgery, Mar. 1980, pp. 338-348, vol. 79, No. 3.

Carter, et al. "Surgical Treatment of Mitral Insufficiency" 1953 (pp. 574-583).

Casselman, et al., "Mitral Valve Surgery Can Now Routinely Be Performed Endoscopically" Downloaded from circ.ahajournals.org, Aug. 26, 2008, pp. 11-48-11-54.

Cauchemez, et al., "High-Flow Perfusion of Sheaths for Prevention of Thromboembolic Complications During Complex Catheter Ablation in the Left Atrium," Journal of Cardiovascular Electrophysiology, Mar. 2004, pp. 276-283, vol. 15, No. 3.

Clinical Trials.gov, Comparing the Effectiveness of a Mitral Valve Repair Procedure in Combination With Coronary 3 Artery Bypass Grafting (CABG) Versus CABG Alone in People with Moderate Ischemic Mitral Regurgitation, http://clinicaltrials.gov/ct2/show/record/NCT00806988?term=mitral+repair&rank=7, Feb. 24, 2009, 1-3.

Clinical Trials.gov, Safety and Efficacy Study of the PTMA Device to Reduce Mitral Valve Regurgitation in Patients With Heart Failure (PTOLEMY2Canada), hllp:I/clinicaltrials.gov/ct2/show/study/NCT00815386?term=Viacor&rank=3, 1-3, Aug. 25, 2008, pp. 1-4.

Clinical Trials.gov, Study of Safety and Efficacy of the Percutaneous Reduction of Mitral Valve Regurgitation in Heart Failure Patients (PTOLEMY-2), hllp:I/clinicaltrials.gov/ct2/show/NCT00787293?term=Viacor&rank=5, 1-2, Aug. 25, 2008, pp. 1-3.

ClinicaiTrials.gov, Aachen Safety and Efficacy of the Percutaneous Transvenous Mitral Annuloplasty Device to Reduce Mitral Regurgitation (PTOLEMY), http://clinicaltrials.gov/ct2/show/NCT00572091 ?term=mitral+regurgitation&rank=2, Aug. 25, 2008, 1-3.

ClinicalTrials.gov, Feasibility Study of a Percutaneous Mitral Valve Repair System., http://clinicaltrials.gov/ct2/show/NCT00209339?term=mitral+valve&rank=3, Aug. 25, 2008, 1-4.

ClinicalTrials.gov, Montreal Safety and Efficacy of the Percutaneous Transvenous Mitral Annuloplasty Device (PTOLEMY), http://clinicaltrials.gov/ct2/show/NCT0057161O?term=mitral+regurgitation&rank=13, Aug. 25, 2008, 1-4.

ClinicalTrials.gov, Pivotal Study of a Percutaneous Mitral Valve Repair System, http://clinicaltrials.gov/ct2/show/NCT00209274?term=mitral+valve&rank=1, Aug. 25, 2008, 1-4.

ClinicalTrials.gov, Restor-MV: Randomized Evaluation of a Surgical Treatment for Off-Pump Repair of the Mitral Valve, http://clinicaltrials.gov/ct2/show/NCT00120276?term=myocor&rank=1, Aug. 25, 2008, 1-5.

ClinicalTrials.gov, Safety and Efficacy of the Percutaneous Transvenous Mitral Annuloplasty Device to Reduce Mitral Regurgitation (PTOLEMY), http://clinicaltrials.gov/ct2/show/NCT00568230?term=mitral+valve&rank=53, Aug. 25, 2008, 1-3.

ClinicalTrials.gov, Vivid-Valvular and Ventricular Improvement Via iCoapsys Delivery-Feasibility Study, http:// clinicaltrials.gov/ct2/show/NCT00512005?term=mitral+valve&rank=12, Aug. 25, 2008, 1-4.

Cohen, Trans-Septal Technique for Tandemheart Insertion, Lenox Hill Heart and Vascular Institute of New York, Barcelona May 22-May 25, 2007, 18 pages.

Corbisiero, et al., "Does Size Really Matter?" A Comparison of the Riata Lead Family Based on Size and Its Relation to Performance, Pace, Jun. 2008, vol. 31, pp. 722-726.

Crabtree, et al., "Recurrent Mitral Regurgitation and Risk Factors for Early and Late Mortality After Mitral Valve Repair for Functional Ischemic Mitral Regurgitation," The Society of Thoracic Surgeons, 2008, pp. 1537-1543, vol. 85.

Criber, et al., "Early Experience With Percutaneous Transcatheter Implantation of Heart Valve Prosthesis for the Treatment of End-Stage Inoperable Patients With Calcific Aortic Stenosis," Journal of the American College of Cardiology, Feb. 18, 2004, pp. 698-703, vol. 43, No. 4.

Criber, et al., "Treatment of Calcific Aortic Stenosis With The Percutaneous Heart Valve- Mid-Term Follow-Up From the Initial Feasibility Studies: The French Experience," Journal of the American College of Cardiology, Mar. 21, 2006, vol. 47, No. 6, pp. 1241-1223.

Danik, et al., "Timing of delayed perforation with the St. Jude Riata lead: A single-center experience and a review of the literature," Heart Rhythm Society, Dec. 2008, vol. 5, No. 12, pp. 1667-1672.

De Bonis, et al., "Similar long-term results of mitral valve repair for anterior compared with posterior leaflet prolapse," The Journal of Thoracic and Cardiovascular Surgery, Feb. 2006, pp. 364-370, vol. 131, No. 2.

Deloche, et al., "Valve repair with Carpentier techniques The second decade," The Journal of Thoracic and Cardiovascular Surgery, Jun. 1990, pp. 990-1002, vol. 99, No. 6.

Del Valle-Fernandez, et al., "Transcatheter heart valves for the treatment of aortic stenosis: state-of-the-art," Minerva Cardioangiologica, Oct. 2008, vol. 56, No. 5, pp. 543-556.

De Simone, et al. "A clinical study of annular geometry and dynamics in patients with ischemic mitral regurgitation: new insights into asymmetrical ring annuloplasty," European Journal of Cardio-thoracic Surgery, 2006, pp. 355-361, vol. 29.

Detaint, et al. "Surgical Correction of Mitral Regurgitation in the Elderly- Outcomes and Recent Improvements," Downloaded from circ.ahajournals.org, Aug. 26, 2008, pp. 265-272.

Douthiti, Cardiac Dimensions® Inc. Receives CE Mark for CARILLQWN Mitral Contour SystemTM, Cardiac Dimensions—News, htpp:I/www.cardiacdimensions.com/usa/press-release-2-4-09.html, downloaded Feb. 24, 2009, pp. 1-2.

Dubreuil, et al., "Percutaneous Mitral Valve Annuloplasty for Ischemic Mitral Regurgitation: First in Man Experience With a Tempory Implant," Catheterization and Cardiovascular Interventions, 2007, pp. 1053-1061, vol. 69.

Duffy, et al., "Feasibility and Short-Term Efficacy of Percutaneous Mitral Annular Reduction for the Therapy of Funcitonal Mitral Regurgitation in Patients With Heart Failure," Catheterization and Cardiovascular Interventions, 2006, pp. 205-210, vol. 68.

Dvorin, Endovalve Inc., Pioneering percutaneous mitral valve replacement, Start-Up Windhover's Review of Emerging Medical Ventures, Jun./Jul. 2006, vol. 11, No. 7, pp. 1-2.

Eisenhauer, et al., "Closure of Prosthetic Paravalvular Mitral Regurgitation With the Gianturco-Grifka Vascular Occlusion Device," Catheterization and Cardiovascular Interventions, 2001, 5 pages, vol. 54.

El Tchaninoff, "Clinical results of percutaneous aortic valve implantation," Euro PCR07, Cribier-Edwards, 30 pages.

Epstein, et al., "Gross and Microscopic Pathological Changes Associated With Nonthoracotomy Implantable Defibrillator Leads," Downloaded from circ.ahajournals.org, Jul. 23, 2008, pp. 1517-1524.

Epstein, et al., "Embolic Complications Associated With Radiofrequency Catheter Ablation," The American Journal of Cardiology, Mar. 15, 1996, pp. 655-658, vol. 77.

European Examination Report dated Aug. 11, 2011 issued in European Patent No. 08 755 418.4, 3 pages.

European Examination Report dated Aug. 4, 2011 issued in European Patent No. 06 816 336.9, 3 pages.

European Search Report dated Jul. 12, 1984 cited in EP0125393.

(56) References Cited

OTHER PUBLICATIONS

European Intent to Grant dated Feb. 22, 2013 issued in Europe Patent Application No. 08 755 418.4, 7 pages.
European Search Report dated Mar. 6, 2013 issued in European Patent Application No. 10804952.9, 8 pages.
European Office Action dated Nov. 7, 2013 issued in European Patent Application No. 10 804 952.9 (5 pages).
Evalve reports 1st MitraClip treatments in the Netherlands, Medical Device Daily, Feb. 19, 2009, vol. 13, No. 32, 2 pages.
Extended European search report dated Nov. 30, 2010 issued in European Patent Application No. 08850467.5, 6 pages.
Extended European search report dated Nov. 30, 2010 issued in European Patent Application No. 08755418.4, 7 pages.
Extended European search report dated Nov. 30, 2010 issued in European Patent Application No. 08849442.2, 6 pages.
Extended European Search Report dated Dec. 1, 2010 issued in European Patent Application No. 08755426.7, 6 pages.
Extended European Search Report dated Dec. 14, 2010 issued in European Patent Application No. 06816336.9, 7 pages.
Fagundes, et al., "Safety of Single Transseptal Puncture for Ablation of Atrial Fibrillation: Retrospective Study from a Large Cohort of Patients," Journal of Cardiovascular Electrophysiology, Dec. 2007, pp. 1277-1281, vol. 18, No. 12.
Feldman, et al., "Patient selection for percutaneous mitral valve repair: insight from early clinical trial applications," Nature Clinical Practice Cardiovascular Medicine, Feb. 2008, 84-90, vol. 5, No. 2.
Feldman, et al. "Percutaneous Mitral Valve Repair Using the Edge-to-Edge Technique- Six-Month Results of the EVEREST Phase I Clinical Trial," Journal of the American College of Cardiology, Dec. 6, 2005, pp. 2134-2140, vol. 46, No. 11.
Fernandez, et al. "Early and late-phase events after valve replacement with the St. Jude Medical prosthesis in 1200 patients," The Journal of Thoracic and Cardiovascular Surgery, Feb. 1994, pp. 394-407, vol. 107, No. 2.
Fitts, et al., "Fluoroscopy-Guided Femoral Artery Puncture Reduces the Risk of PCI-Related Vascular Complications," Journal of Interventional Cardiology, vol. 21, No. 3, 2008, pp. 273-278.
French catheter scale chart http://en.wikipedia.org/wiki/French_catheter_scale_chart, Dec. 20, 2006, 1 page.
Fukuda, et al., "Maintenance of Geometric Alterations Associated with Percutaneous Mitral Valve Repair: Real-Time Three-Dimensional Echocardiographic Assessment in an Ovine Model," J. Heart Valve Dis, May 2008, vol. 17, No. 3, 276-282.
Gelsomino, et al. "Left ventricular diastolic function after restrictive mitral ring annuloplasty in chronic ischemic mitral regurgitation and its predictive value on outcome and recurrence of regurgitation," International Journal of Cardiology, vol. 132,2009, pp. 419-428.
General Physical Properties of PVA Sponge (values are not guaranteed), Ceiba Technologies, http://www.ceibatech.com/PVASpongeDate.htm, Dec. 20, 2006 3 pages.
Geyfman, et al. "Cardiac Tamponade as Complication of Active-Fixation Atrial Lead Perforations: Proposed Mechanism and Management Algorithm," PACE, Apr. 2007, vol. 30, pp. 498-501.
Gillinov, et al. "Durability of Mitral Valve Repair for Degenerative Disease," The Journal of Thoracic and Cardiovascular Surgery, Nov. 1998, pp. 734-743, vol. 116, No. 5.
Glenn, et al., "The Surgical Treatment of Mitral Insufficiency with Particular Reference to the Application of a Vertically Suspended Graft," Jul. 1956, pp. 59-77.
Glenn, et al., "The Implantation of a Vascularized Graft in the Chambers of the Heart," 1954, pp. 5-11.
Glenn, et al., "The Surgical Treatment of Mitral Insufficiency: the Fate of a Vascularized Transchamber Intracardiac Graft," Apr. 1955, pp. 510-518.
Glover, et al., "The Fate of Intracardiac Pericardia! Grafts as Applied to the Closure of Septal Defects and to the Relief of Mitral Insufficiency" 1952, pp. 178-185.

Gorman, et al., "Surgical Therapy for Mitral Regurgitation: The Key to Preventing Heart Failure," Prevention of Heart Failure After Myocardial Infarction, 2008, pp. 211-215.
Grossi, et al., "Intraoperative Effects of the Coapsys Annuloplasty System in a Randomized Evaluation (RESTOR- MV) of Functional Ischemic Mitral Regurgitation," The Society of Thoracic Surgeons, 2005, pp. 1706-1711, vol. 80.
Grossi, et al., "Late Results of Mitral Valve Reconstruction in the Elderly," The Society of Thoracic Surgeons, 2000, pp. 1224-1226, vol. 70.
Gross, et al. "Minimally Invasive Mitral Valve Surgery: A 6-Year Experience With 714 Patients," The Society of Thoracic Surgeons, 2002, pp. 660-6604, vol. 74.
Harken, et al., "The Surgical Treatment of Mitral Insufficiency," The Journal of Thoracic Surgery, pp. 604-627 (1954).
Harken, et al., "The Surgical Correction of Mitral Insufficiency" 1953, pp. 4-7.
Harper, Evalve Announces Enrollment Completion of the Everest Randomized Study, http://www.evalveinc.com/ europe/press/17.html, downloaded Feb. 24, 2009, pp. 1-3.
Harper, Two-Year Follow-Up Data Demonstrates Preservation of Adequate Mitral Valve Area in Patients Treated with the MitraCiip®-system, http://www.evalveinc.com/europe/press/21.html, downloaded Feb. 24, 2009, pp. 1-3.
Henderson, et al., "The Surgical Treatment of Mitral Insufficiency" Jun. 1953, pp. 858-868.
Hendren, et al., "Mitral Valve Repair for Ischemic Mitral Insufficiency," The Society of Thoracic Surgeons, 1991, pp. 1246-1252, vol. 52.
Heupler, et al. "Infection Prevention Guidelines for Cardiac Catheterization Laboratories," Catheterization and Cardiovascular Diagnosis, 1992, pp. 260-263, vol. 25.
Hourihan et al., "Transcatheter Umbrella Closure of Valvular and Paravalvular Leaks," American College of Cardiology, Nov. 15, 1992, 7 pages, vol. 20, No. 6.
Hung, et al., "3D Echocardiography: A Review of the Current Status and Future Directions, ASE Position Paper," Journal of the American Society of Echocardiography, Mar. 2007, pp. 213-233.
Hung, et al., "Mechanism of Dynamic Regurgitant Orifice Area Variation of Functional Mitral Regurgitation-Physiologic Insights From the Proximal Flow Convergence Technique," Journal of the American College of Cardiology, Feb. 1999, vol. 33, No. 2, pp. 538-545.
Hung, et al., "A Novel Approach for Reducing Ischemic Mitral Regurgitation by Injection of a Polymer of Reverse Remodel and Reposition Displaced Papillary Muscles, Circulation," Journal of the American Heart Association, Sep. 30, 2008, Downloaded from circ.ahajournals.org at National Insthealth Lib on Feb. 25, 2009, S262-S269.
Hvass, et al., "Papillary Muscle Sling: A New Functional Approach to Mitral Repair in Patients With Ischemic Left Ventricular Dysfunction and Functional Mitral Regurgitation," The Society of Thoracic Surgeons, 2003, pp. 809-811, vol. 75.
Hytowitz, "First U.S. Patients Enrolled in the Realism Continued Access Study, evalve, http://www.evalveinc.com/ europe/press/22/html," downloaded Feb. 24, 2009, 2 pages.
Ibrahim, et al. "The St. Jude Medical prosthesis- A thirteen-year experience," The Journal of Thoracic and Cardiovascular Surgery, Aug. 1994, 221-230, vol. 108, No. 2.
Intent to Grant dated Jan. 2, 2013 issue in European Patent Application No. 06816336.9, 7 pages.
International Search Report and Written Opinion dated Sep. 22, 2008 issued in PCT Application No. PCT/US08/63560 11 pages.
International Search Report and Written Opinion dated Sep. 29, 2008 issued in PCT Application No. PCT/US08/63568 12 pages.
International Preliminary Report on Patentability dated Jan. 31, 2012 issued in PCT Patent Application No. PCT/ US2010/043360, 7 pages.
International Search Report and Written Opinion dated Feb. 25, 2009 issued in PCT Application No. PCT/ US08/083570, 13 pages.
International Search Report and Written Opinion dated Apr. 2, 2009 issued in PCT Application No. PCT/US08/083574, 8 pages.

(56) References Cited

OTHER PUBLICATIONS

International Search Report and Written Opinion dated Jul. 6, 2010 issued in PCT Patent Application No. PCT/US2010/032764, 9 pages.
International Search Report and Written Opinion, dated May 11, 2007 (6 pages) filed in corresponding PCT application PCT/US06/39011 (8 pages).
International Search Report and Written Opinion dated Jan. 16, 2009 issued in PCT Application No. PCT/US08/83497 10 pages.
International Search Report and Written Opinion dated Sep. 21, 2010 issued in PCT Patent Application No. PCT/US201 0/043360, 9 pages.
International Search Report and Written Opinion dated Aug. 11, 2009 issued in PCT Application No. PCT/ US2009/046995, 11 pages.
Iskandar, et al., "Tricuspid Valve Malfunction and Ventricular Pacemaker Lead: Case Report and Review of the Literature," Echocardiography: A Journal of CV Ultrasound & Allied Tech., 2006, pp. 692-697, vol. 23, No. 8.
Jilaihawi, et al., "Percutaneous Aortic Valve Replacement in Patients with Challenging Aortoiliofemoral Access," Catheterization and Cardiovascular Interventions, 2008, vol. 72, pp. 885-890.
Johns, et al., "Mitral Insufficiency: the Experimental Use of a Mobile Polyvinyl Sponge Prosthesis," Annals of Surgery, Sep. 1954, pp. 335-341.
Jovin, et al. "Atrial Fibrillation and Mitral Valve Repair," Pace, Aug. 2008, vol. 31, pp. 1057-1063.
Kahlert, et al., "Direct Assessment of Size and Shape of Noncircular Vena Contracta Area in Functional Versus Organic Mitral Regurgitation Using Real-Time Three-Dimensional Echocardiography, Valvular Heart Disease," Journal of the American Society of Echocardiography, Aug. 2008, vol. 21, No. 8, pp. 912-921.
Kasegawa, et al., "Mitral Valve Repair for Anterior Leaflet Prolapse With Expanded Polytetraftuoroethylene Sutures," The Society of Thoracic Surgeons, 2006, pp. 1625-1631, vol. 81.
Kaye, et al., "Feasibility and Short-Term Efficacy of Percutaneous Mitral Annular Reduction for the Therapy of Heart Failure-Induced Mitral Regurgitation," Downloaded from circ.ahajournals.org, Aug. 26, 2008, pp. 1795-1797.
Kempfert, et al., "Minimally invasive off-pump valve-in-a-valve implantation: the atrial transcatheter approach for re- operative mitral valve replacement," European Heart Journal, 2008, vol. 29, pp. 2382-2387.
Kerensky, Complications of Cardiac Catheterization and Strategies to Reduce Risks, Diagnostic and Therapeutic Cardiac Catheterization, 1998, Chapter 8, pp. 91-105.
Kodali, et al., "Transcatheter Valve Repair and Replacement," Downloaded from arjournals.annualreviews.org by National Institute of Health Library on Feb. 25, 2009, 14 pages.
Koertke, et al. "INR Self-Management Permits Lower Anticoagulation Levels After Mechanical Heart Valve Replacement," downloaded from circ.ahajournals.org, Aug. 26, 2008, pp. 11-75-11-78.
Kratz, et al., "St. Jude Prosthesis for Aortic and Mitral Valve Replacement: A Ten-Year Experience," The Society of Thoracic Surgeons, 1993, pp. 462-468, vol. 56.
Kron, et al., "Surgical Relocation of the Posterior Papillary Muscle in Chronic Ischemic Mitral Regurgitation," The Society of Thoracic Surgeons, 2002,pp. 600-601, vol. 74.
Kuck, et al. "Best of Structural Heart Disease Abstracts, TCT-124" The American Journal of Cardiology, Oct. 20-25, 2007, pp. 56L-59L.
Kuwahara, et al., "Mechanism of Recurreni/Persistent Ischemic/Functional Mitral Regurgitation in the Chronic Phase After Surgical Annuloplasty—Importance of Augmented Posterior Leaftet Tethering," Circulation, Jul. 4, 2006, pp. 1-529-1-534.
Kwan, et al., "Geometric Differences of the Mitral Apparatus Between Ischemic and Dilated Cardiomyopathy With Significant Mitral Regurgitation- Real-Time Three-Dimensional Echocardiography Study," Circulation, Mar. 4, 2003, pp. 1135-1140.
Laskey, et al., "Multivariable Model for Prediction of Risk of Significant Complication During Diagnostic Cardiac Catheterization," Catheterization and Cardiovascular Diagnosis, 1993, pp. 185-190, vol. 30.
Lee, et al., "Mitral Valve Reconstruction: Experience Related to Early and Late Mortality and Reoperation," J Heart Valve Dis, Nov. 2005, pp. 715-721, vol. 14, No. 6.
Leung, et al., "Percutaneous Mitral Valve Repair—An overview of the current devices and techniques," Coronary/Cardiac Interventions- Endovascular Today, Oct. 2006, pp. 26-33.
Levine, et al., "Mechanistic Insights into Functional Mitral Regurgitation," Valvular Heart Disease, 2009, pp. 125-129.
Liddicoat, et al., "Percutaneous Mitral Valve Repair: A Feasibility Study in an Ovine Model of Acute Ischemic Mitral Regurgitation," Catheterization and Cardiovascular Interventions, 2003, pp. 410-416, vol. 60.
Lim, et al., "Percutaneous Transthoracic Ventricular Puncture for Diagnostic and Interventional Catheterization," Catheterization and Cardiovascular Interventions, 2008, pp. 915-918, vol. 71.
Lin, et al., "Severe Symptomatic Tricuspid Valve Regurgitation Due to Permanent Pacemaker or Implantable Cardioverter-Defibrillator Leads," Journal of the American College of Cardiology, May 17, 2005, pp. 1672-1675, vol. 45, No. 10.
Little, et al., "Three-Dimensional Ultrasound Imaging Model of Mitral Valve Regurgitation: Design and Evaluation," Ultrasound in Medicine and Biology, 2008, vol. 34, No. 4, pp. 647-654.
Llaneras, et al., "Large Animal Model of Ischemic Mitral Regurgitation," The Society of Thoracic Surgeons—Ischemic Mitral Insufficiency, 1994, vol. 57, pp. 432-439.
Lozonschi, et al., "Transapical Mitral Valved Stent Implantation," The Society of Thoracic Surgeons, 2008, pp. 745-748, vol. 86.
Mack, "Percutaneous Therapies for Mitral Regurgitation: Where Do We Stand and Where Are We Going? Do Current Devices Really Represent a Step Forward Compared to Surgery?," Heart Valve Summit, Jun. 7, 2007, 59 pages.
Magne, et al., "Ischemic Mitral Regurgitation: A Complex Multifaceted Disease," Cardiology, 2009, vol. 112, pp. 244-259.
Maleki, et al., "Intracardiac Ultrasound Detection of Thrombus on Transseptal Sheath: Incidence, Treatment, and Prevention," Journal of Cardiovascular Electrophysiology, Jun. 2005, pp. 561-565, vol. 16, No. 6.
Maniu, et al., "Acute and Chronic Reduction of Functional Mitral Regurgitation in Experimental Heart Failure by Percutaneous Mitral Annuloplasty," Journal of the American College of Cardiology, Oct. 19, 2004, pp. 1652-1661, vol. 44, No. 8.
Matthews, Anatomy of the Heart, Definitions Cardiology Explained and Presented by Robert Matthews, MD, http:!/ www.rjmatthewsmd.com/Definitions/anatomy_ofthe_heart.htm, printed Jul. 28, 2008, 265 pages.
McClure, et al., "Early and late outcomes in minimally invasive mitral valve repair: An eleven-year experience in 707 patients, Acquired Cardiovascular Disease," The Journal of Thoracic and Cardiovascular Surgery, Jan. 2009, vol. 137, No. 1, pp. 70-75.
McGee, et al., "Recurrent mitral regurgitation after annuloplasty for functional ischemic mitral regurgitation, Surgery for Acquired Cardiovascular Disease," The Journal of Thoracic and Cardiovascular Surgery, Dec. 2004, pp. 916-924.e4, vol. 128, No. 6.
Mehra, et al., "Surgery for Severe Mitral Regurgitation and Left Ventricular Failure: What Do We Really Know?," Journal of Cardiac Failure, Mar. 2008, pp. 145-150. vol. 14, No. 2.
Menicanti, et al. "Functional Ischemic Mitral Regurgitation in Anterior Ventricular Remodeling: Results of Surgical Ventricular Restoration with and Without Mitral Repair," Heart Failure Reviews, 2004, pp. 317-327, vol. 9.
Messas, et al., "Efficacy of Chordal Cutting to Relieve Chronic Persistent Ischemic Mitral Regurgitation," Circulation, Sep. 9, 2003, pp. 11-111-11-115.
Meurin, et al., "Thromboembolic events early after mitral valve repair: Incidence and predictive factors," International Journal of Cardiology, 2008, pp. 45-52, vol. 126.
Mirable, et al., "What are the characteristics of patients with severe, symptomatic, mitral regurgitation who are denied surgery?," The European Society of Cardiology, 2007, pp. 358-365, vol. 28.

(56) References Cited

OTHER PUBLICATIONS

Mitchell, et al., "Complications, Cardiac catheterization and coronary intervention," Chapter 9, 2008, pp. 238-270.
Mishra, et al., "Coapsys Mitral Annuloplasty for Chronic Functional Ischemic Mitral Regurgitation: 1-Year Results," The Society of Thoracic Surgeons, 2006, pp. 42-46, vol. 81.
Modi, et al., "Minimally invasive mitral valve surgery: a systematic review and meta-analysis," European Journal of Cardia-Thoracic Surgery, 2008, vol. 34, pp. 943-952.
Moore, et al., "Unsuitability of Transventricular Autogenous Slings for Diminishing Valvular Insufficiency," Feb. 1953, pp. 173-182.
Morgan, et al., "Left Heart Catheterization by Direct Ventricular Puncture: Withstanding the Test of Time," Catheterization and Cardiovascular Diagnosis, 1989, pp. 87-90, vol. 16.
Moscucci, et al., "Coil Embolization of a Periprosthetic Mitral Valve Leak Associated With Severe Hemolytic Anemia, Images in Cardiovascular Medicine," American Heart Association, Inc., 2001, 2 pages, vol. 104.
Mullins, "Flow directed catheters ("floating" balloon catheters), Cardiac Catheterization in Congenital Heart Disease," Pediatric and Adult, 2006, Chapter 7, pp. 213-221, 9 pages, Blackwell Futura, USA.
Mullins, "Vascular access. Cardiac Catheterization in Congenital Heart Disease," Pediatric and Adult, 2006, Chapter 4, pp. 115-117, 5 pages, Blackwell Futura, USA.
Mullins, "Aortic valve dilation, Cardiac Catheterization in Congenital Heart Disease," Pediatric and Adult, 2006, Chapter 19, pp. 487-489, 5 pages, Blackwell Futura, USA.
Mullins, "Foreign body removal, Cardiac Catheterization in Congenital Heart Disease," Pediatric and Adult, 2006, Chapter 12, pp. 350-377, 30 pages, Blackwell Futura, USA.
Murday, et al., "A Prospective Controlled Trial of St. Jude Versus Starr Edwards Aortic and Mitral Valve Prostheses," The Society of Thoracic Surgeons, 2003, pp. 66-74, vol. 76.
Myers, Jr., et al., "Color Doppler Velocity Accuracy Proximal to Regurgitant Orifices: Influence of Orifice Aspect Ratio," Ultrasound in Medicine and Biology, 1999, vol. 25, No. 5, pp. 771-792.
Nifong, et al., "Robotic mitral valve surgery: A United States multicenter trial," The Journal of Thoracic and Cardiovascular Surgery, Jun. 2005, pp. 1395-1404, vol. 129, No. 6.
Ning, et al., "Live three-dimensional transesophageal echocardiography in mitral valve surgery," Chinese Medical Journal, 2008, vol. 121, No. 20, pp. 2037-2041.
Noto, et al., "Cardiac Catheterization 1990: A Report of the Registry of the Society for Cardiac Angiography and Interventions (SCA &I)," Catheterization and Cardiovascular Diagnosis, 1991, pp. 75-83, vol. 24.
Notzold, et al., "Microemboli in aortic valve replacement," Future Drugs Ltd, Expert Rev. Cardiovasc. Ther., vol. 14, No. 6, 2006, pp. 853-859.
Ohlow, et al., "Incidence and outcome of femoral vascular complications among 18,165 patients undergoing cardiac catheterisation," International Journal of Cardiology, 2008, pp. 1-6.
Onundarson, et al., "Warfarin anticoagulation intensity in specialist-based and in computer-assisted dosing practice," International Journal of Laboratory Hematology, 2008, vol. 30, pp. 382-389.
Otsuji, et al., "Insights From Three-Dimensional Echocardiography Into the Mechanism of Functional Mitral Regurgitation- Direct in Vivo Demonstration of Altered Leaflet Tethering Geometry," Circulation, Sep. 16, 1997, vol. 96, No. 6, pp. 1999-2008.
Pai et al., "Effect of Atrial Fibrillation on the Dynamics of Mitral Annular Area," J. Heart Valve Dis., Jan. 2003, vol. 12, No. 1, pp. 31-37.
Palacios, et al. "Safety and Feasibility of Acute Percutaneous Septal Sinus Shortening: First-In-Human Experience," Catheterization and Cardiovascular Interventions, 2007, pp. 513-518.
Paniagua, et al., "First Human Case of Retrograde Transcatheter Implantation of an Aortic Valve Prosthesis, Texas Heart Institute Journal," Transcatheter Aortic Valve Prosthesis, 2005, vol. 32, No. 3, pp. 393-398.

Pedersen, et al. "iCoapsys Mitral Valve Repair System: Percutaneous Implantation in an Animal Model," Catheterization and Cardiovascular Interventions, 2008, pp. 125-131,vol. 72.
Piazza, et al., "Transcatheter Mitral Valve Repair for Functional Mitral Regurgitation: Coronary Sinus Approach," Journal of Interventional Cardiology, 2007, pp. 495-508, vol. 20, No. 6.
Preliminary Report on Patentability dated Nov. 10, 2011 issued in PCT Patent Application No. PCT/ US2010/032764, 4 pages.
Prifti, et al., "Ischemic Mitral Valve Regurgitation Grade II-III: Correction in Patients with Impaired Left Ventricular Function undergoing Simultaneous Coronary Revascularization," J Heart Valve Dis, Nov. 2001, pp. 754-762, vol. 10, No. 6.
PVA Datasheet, www.sponge-pva.com/data.htm. Dec. 20, 2006, 2 pages.
Pva Sponge W (wet) & D (dry), Ceiba Technologies, http://www.ceibatech.com/PVASpongeW&D.htm, Dec. 20, 2007 5 pages.
Rashkind, et al., "Nonsurgical closure of patent ductus arteriosus: clinical application of the Rash kind PDA Occluder System," Therapy and Prevention-Congenital Heart Disease, Mar. 1987, 10 pages, vol. 75, No. 3.
Richardson, et al., "Is a port-access mitral valve repair superior to the sternotomy approach in accelerating postoperative recovery?," Interactive CardioVascular and Thoracic Surgery, Downloaded from icvts.ctsnetjournals.org, Aug. 26, 2008, pp. 670-683, vol. 7.
Rinaldi, et al., "Best of Structural Heart Disease Abstracts, TCT-123," The American Journal of Cardiology, Oct. 20-25, 2007, 57L.
Rodes-Cabau, et al., "Feasibility and Initial Results of Percutaneous Aortic Valve Implantation Including Selection of the Transfemoral or Transapical Approach in Patients With Severe Aortic Stenosis," The American Journal of Cardiology, 2008, pp. 1240-1246.
Ruiz, "New Percutaneous Approaches for Mitral Regurgitation," Lenox Hill Heart and Vascular Institute of New York, May 13-16, 2008, 26 pages.
Rumel, et al., "Section on Cardiovascular Diseases—The Correction of Mitral Insufficiency With a Trans-Valvular Polyvinyl Formalinized Plastic (Ivalon) Sponge Prosthesis," American College of Chest Physicians, Apr. 1958, Downloaded from chestjournal.org, Jul. 23, 2008, pp. 401-413.
Ryhanen, et al, "In vivo biocompatibility evaluation of nickel-titanium shape memory metal alloy: Muscle and perineural tissue responses and encapsule membrane thickness," Jan. 19, 1998, Journal of Biomedical Materials Research, pp. 481-488.
Sakakibara, "A Surgical Approach to the Correction of Mitral Insufficiency" Aug. 1955 (pp. 196-203).
Satpathy, et al., "Delayed Defibrillator Lead Perforation: An Increasing Phenomenon," Pace, Jan. 2008, vol. 31, pp. 10-12.
Schofer, "Percutaneous MVR: Clinical Evaluation," The Carillon Experience, EuroPCR 2007, Barcelona, Spain, May 22-25, 2007, 35 pages.
Schwammenthal, et al., "Dynamics of Mitral Regurgitant Flow and Orifice Area—Physiologic Application of the Proximal Flow Convergence Method: Clinical Data and Experimental Testing," Circulation, Jul. 1994, vol. 90, No. 1, pp. 307-322.
Seeburger, et al. "Minimal invasive mitral valve repair for mitral regurgitation: results of 1339 consecutive patients," European Journal of Cardio-thoracic Surgery, 2008, pp. 1-6.
Siminiak, et al., "Best of Structural Heart Disease Abstracts, TCT-125," The American Journal of Cardiology, Oct. 20-25, 2007, 58L.
Southard, et al., "Current Catheter-Based Treatments of Functional Mitral Regurgitation," Cardiac Interventions Today, Jun. 2007, pp. 41-44.
Spencer, "Viacor, Inc. Announces First Patient Treated in PTOLEMY-2 Study," http://www.viacorinc.com/viacor_news.html, Nov. 14, 2008, downloaded Feb. 24, 2009, 2 pages.
Sterlinski, et al., "Subacute cardiac perforations associated with active fixation leads," Clinical Research Leads and Lead Extraction, Europace, 2009, vol. 11, pp. 206-212.
Svensson, et al., "United States Feasibility Study of Transcatheter Insertion of a Stented Aortic Valve by the Left Ventricular Apex," The Society of Thoracic Surgeons, 2008, pp. 46-55, vol. 86.
SPI-Chem™ Vinylec® (Formvar®) Resins, http://www.2spi.com/catalog/submal/formvar-resins.shtml, Dec. 20, 2006, 5 pages.

(56) References Cited

OTHER PUBLICATIONS

Toledano, et al., "Mitral regurgitation: Determinants for referral for cardiac surgery by Canadian cardiologists," J. Cardiol, Mar. 1, 2007, pp. 209-214, vol. 23, No. 3.
Tops et al., Percutaneous Valve Procedures: An Update, Curr Probl Cardiol, Aug. 2008, pp. 417-426.
Trippel, et al., "Reinforced Ivalon Sponge as an Aortic Prosthesis," Feb. 1960 (9 pages).
Turakhia, et al., "Rates and severity of perforation from implantable cardioverter-defibrillator leads a 4-year study," J Interv. Card Electrophysiol, 2009, vol. 24, pp. 47-52.
Vahanian, "The Cardiologist's Perspective on the Future of Percutaneous Mitral Valve Repair," Euro PCR07, 53 pages (2007).
Vahanian, "Coronary Sinus and Direct Annuloplasty Percutaneous Mitral Valve Repair," Innovations in Cardiovascular Interventions, Dec. 7-9, 2008, Tel-Aviv, Israel, 22 pages.
Vahanian, Edwards MONARC system—Evolution Interim Results, 31 pages. (2007).
Vahanian, "Overview on Percutaneous Mitral Valve Technology, Euro PCR07," Transcatheter Valve Symposium, Barcelona, May 22-25, 2007, 23 pages.
Van Gelder, et al., "Diagnosis and Management of Inadvertently Placed Pacing and ICD Leads in the Left Ventricle: A Multicenter Experience and Review of the Literature," Pace, May 2000, vol. 23, pp. 877-883.
Vinylec® Resins, http://www.2spi.com/catalog/submal/vinylec-physical.html, Dec. 20, 2006, 1 page.
Vranckx, et al., "The Tandem Heart®, percutaneous transseptalleft ventricular assist device: a safeguard in high-risk percutaneous coronary interventions. The six-year Rotterdam experience," Clinical research EuroInterv., 2008, vol. 4, pp. 331-337.
Walther, et al., "Transapical minimally invasive aortic valve implantation; the initial 50 patients," European Journal of Cardio-thoracic Surgery, 2008, pp. 983-988, vol. 33.
Webb, et al., "Percutaneous Mitral Annuloplasty With the MONARC System: Preliminary Results From the Evolution Trial, TCT-103," The American Journal of Cardiology, Oct. 22-27, 2006, 49M.
Webb, et al. "Percutaneous Transvenous Mitral Annuloplasty—Initial Human Experience with Device Implantation in the Coronary Sinus," downloaded from circ.ahajournals.org, Aug. 26, 2008, pp. 851-855.
Webster, et al., "Impact of transvenous ventricular pacing leads on tricuspid regurgitation in pediatric and congenital heart disease patients," J Interv Card Electrophysiol, 2008, pp. 65-68, vol. 21.
Wolf, et al., "Solid and gaseous cerebral micorembolization after biologic and mechanical aortic valve replacement: Investigation with multirange and multifrequency transcranial Doppler ultrasound," The Journal of Thoracic and Cardiovascular Surgery, Mar. 2008, vol. 135, No. 3, pp. 512-520.
Xiangming, et al., "In Vivo Characterization of Attachment Safety Between Cardiac Pacing Lead and Canine Heart Muscle," Acta Mechanica Salida Sinica, Sep. 2007, vol. 20, No. 3, pp. 189-197.
Yamaura, et al., "Geometrical Demonstration and Three-Dimensional Quantitative Analysis of the Mitral Valve With Real-Time Three-Dimensional Echocardiography: Novel Anatomical Image Creation System," J Echocardiogr, 2004, vol. 2, No. 4, pp. 99-104.
Ye, et al., "Six-month outcome of transapical transcatheter aortic valve implantation in the initial seven patients," European Journal of Cardio-thoracic Surgery, 2007, pp. 16-21, vol. 31.
Yosefy, et al., "Proximal Flow Convergence Region as Assessed by Real-time 3-Dimensional Echocardiography: Challenging the Hemispheric Assumption," Journal of the American Society of Echocardiography, April2007, Vol., No. 4, pp. 389-396.
Yoshida, et al., "Assessment of Left-to-Right Atrial Shunting After Percutaneous Mitral Valvuloplasty by Transesophageal Color Doppler Flow-Mapping," Circulation, Dec. 1989, pp. 1521-1526, vol. 80, No. 6.
Zhou, et al., "Thromboembolic Complications of Cardiac Radiofrequency Catheter Ablation: A Review of the Reported Incidence. Pathogenesis and Current Research Directions." Journal of Cardiovascular Electrophysiology, Apr. 1999, pp. 611-620, vol. 10, No. 4.
Office Action received in Chinese Application No. 201480028456.7, dated Oct. 18, 2016; 12 pages.
Office Action received in Chinese Application No. 201480045369.2, dated Sep. 1, 2016; 12 pages.
Office Action received in Chinese Application No. 201480028344.1, dated Nov. 15, 2016; 10 pages.
Extended EuropeanSearch Report dated Oct. 7, 2016 issued in European Patent Application No. 14769641.3; 8 pages.
Extended European Search Report dated Oct. 10, 2016 issued in European Patent Application No. 14770314.4; 8 pages.

IMPLANT DELIVERY SYSTEM AND METHOD

CROSS-REFERENCE TO RELATED APPLICATIONS

The present application is a divisional of U.S. patent application Ser. No. 11/940,694, filed on Nov. 15, 2007, which is incorporated by reference herein in its entirety.

FIELD OF THE APPLICATION

The present disclosure relates to the repair and/or correction of dysfunctional heart valves, and more particularly pertains to heart valve implants and systems and methods for delivery and implementation of the same.

BACKGROUND

A human heart has four chambers, the left and right atrium and the left and right ventricles. The chambers of the heart alternately expand and contract to pump blood through the vessels of the body. The cycle of the heart includes the simultaneous contraction of the left and right atria, passing blood from the atria to the left and right ventricles. The left and right ventricles then simultaneously contract forcing blood from the heart and through the vessels of the body. In addition to the four chambers, the heart also includes a check valve at the upstream end of each chamber to ensure that blood flows in the correct direction through the body as the heart chambers expand and contract. These valves may become damaged, or otherwise fail to function properly, resulting in their inability to properly close when the downstream chamber contracts. Failure of the valves to properly close may allow blood to flow backward through the valve resulting in decreased blood flow and lower blood pressure.

Mitral regurgitation is a common variety of heart valve dysfunction or insufficiency. Mitral regurgitation occurs when the mitral valve separating the left coronary atrium and the left ventricle fails to properly close. As a result, upon contraction of the left ventricle blood may leak or flow from the left ventricle back into the left atrium, rather than being forced through the aorta. Any disorder that weakens or damages the mitral valve can prevent it from closing properly, thereby causing leakage or regurgitation. Mitral regurgitation is considered to be chronic when the condition persists rather than occurring for only a short period of time.

Regardless of the cause, mitral regurgitation may result in a decrease in blood flow through the body (cardiac output). Correction of mitral regurgitation typically requires surgical intervention. Surgical valve repair or replacement is carried out as an open heart procedure. The repair or replacement surgery may last in the range of about three to five hours, and is carried out with the patient under general anesthesia. The nature of the surgical procedure requires the patient to be placed on a heart-lung machine. Because of the severity/complexity/danger associated with open heart surgical procedures, corrective surgery for mitral regurgitation is typically not recommended until the patient's ejection fraction drops below 60% and/or the left ventricle is larger than 45 mm at rest.

BRIEF DESCRIPTION OF DRAWINGS

Features and advantage of the claimed subject matter will be apparent from the following description of embodiments consistent therewith, which description should be considered in conjunction with the accompanying drawings, wherein:

DESCRIPTION

Figure 1:
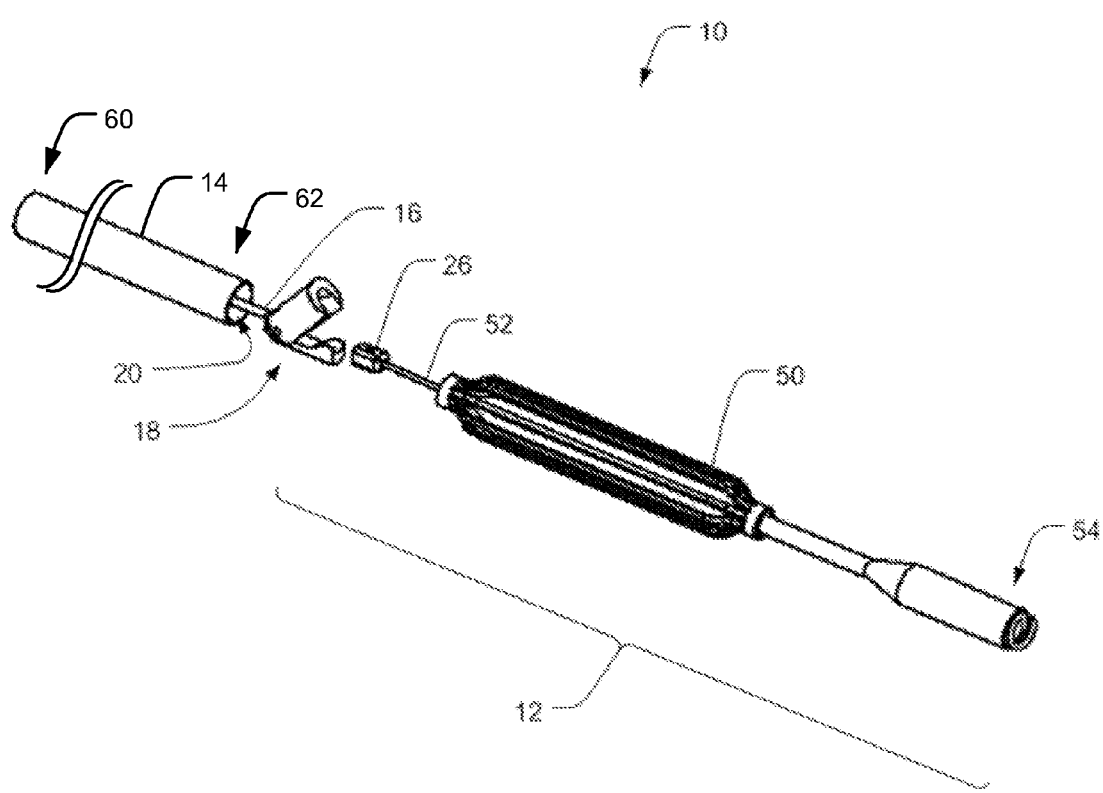
FIG. 1 is a perspective view of one embodiment of a mitral valve implant delivery system.

Referring to FIG. 1, a perspective view of one embodiment of a percutaneous delivery system 10 for delivering and/or recapturing a mitral valve implant 12 within the heart is shown. The delivery system 10 may include a mitral valve implant 12, a catheter 14 and a guide wire 16 having a clamping mechanism 18 configured to be releasably coupled to the mitral valve implant 12 as will be explained in greater detail hereinbelow.

As shown, the delivery system 10 may include a catheter 14 configured to be percutaneously introduced or inserted into one or more vessels of the body (e.g., one or more veins and/or arteries) and conveyed to the heart for delivery and/or recapture of the mitral valve implant 12. Conveyance of the catheter 14 and/or of the mitral valve implant 12 to the heart may be directed and/or assisted by monitoring the travel of the catheter 14, e.g., via radiographic and/or other imaging techniques and/or by passing the catheter 14 through another, larger catheter already in place (not shown). The catheter 14 may have a length and outer diameter configured to extend from the incision site in the patient's body through one or more veins and/or arteries to the desired location within the heart (e.g., the left ventricle). Additionally, the catheter 14 may define at least one lumen 20 having an internal diameter configured to receive and convey the guide wire 16, the clamping mechanism 18 and the implant 12 from a first end 60 of the catheter 14 to a second end 62 of the catheter 14. The catheter 14 may include a flexible material having sufficient rigidity, strength and inner lubricity to be guided through the blood vessels to the heart and to convey the implant 12. For example, the catheter 14 may include a combination or combinations of polymeric and/or metallic materials having an inner diameter of between 5 French size and 50 French size, an outer diameter of between 0.004 inches 0.250 inches larger than the corresponding inner diameter, and a length of between 10 centimeters and 200 centimeters.

The guide wire 16 may be configured to be disposed within the lumen 20 of the catheter 14 and may have a length greater than the length of the catheter 14. The guide wire 16 may include a flexible wire having sufficient strength and/or rigidity to convey and/or urge the implant 12 through the lumen 20 of the catheter 14. For example, the guide wire 16 may include a combination or combinations of polymeric and/or metallic materials having a diameter of between 0.004 inches and 0.060 inches and a length of between 100 centimeters and 500 centimeters.

Figure 2:
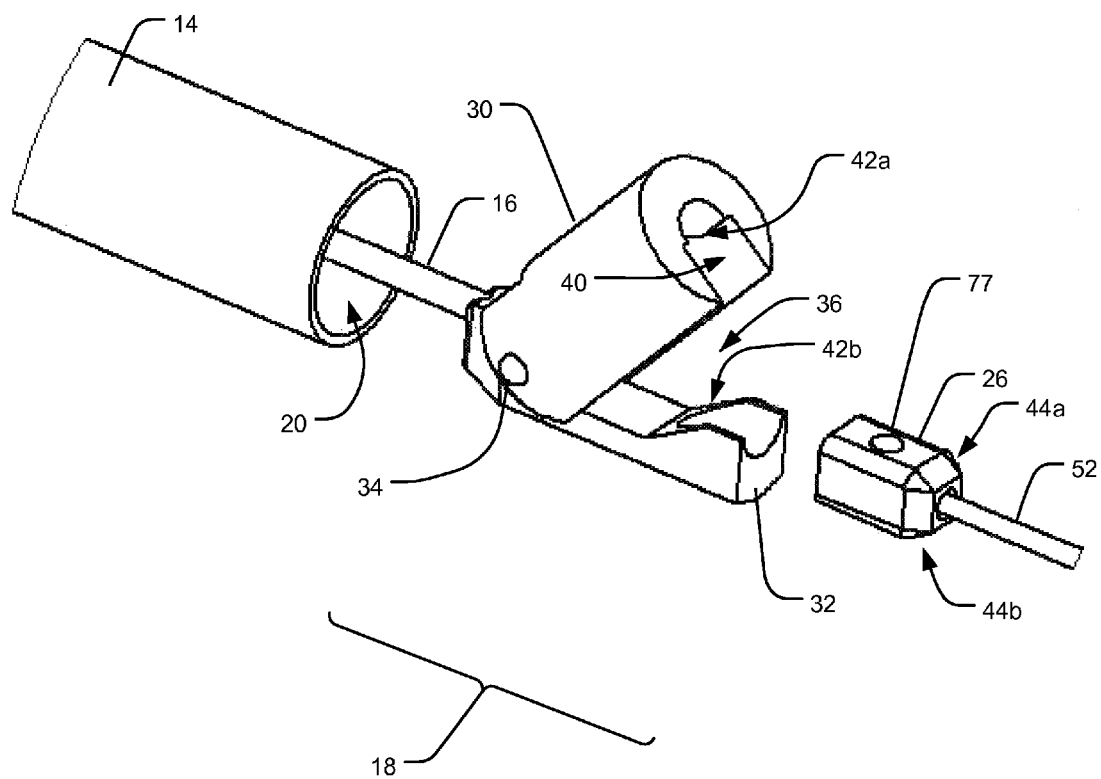
FIG. 2 depicts one embodiment of a clamping mechanism and driver in an open position.
Figure 3:
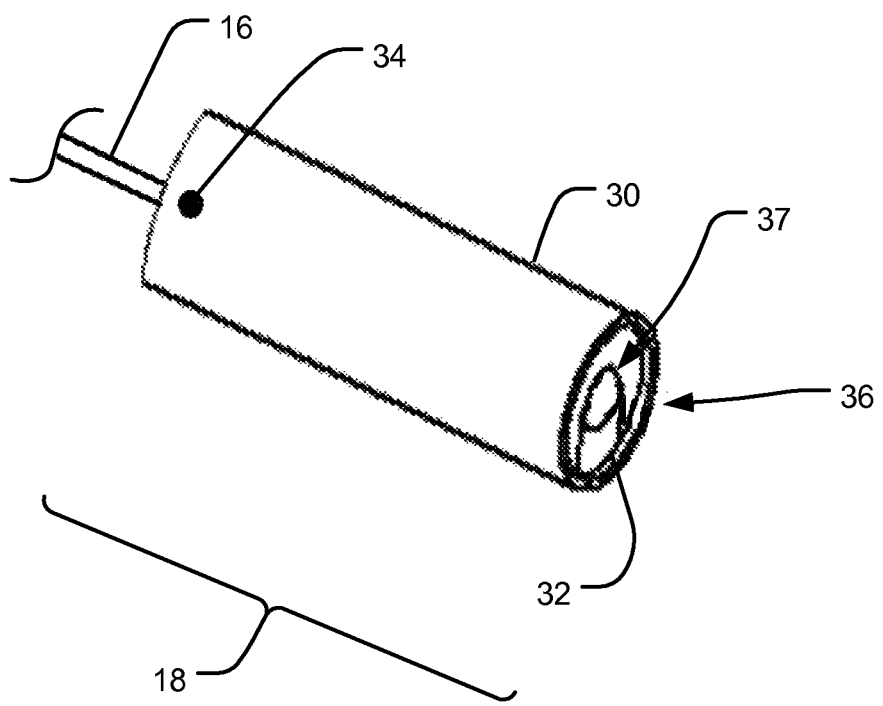
FIG. 3 depicts one embodiment of a clamping mechanism and driver in a closed position.

A distal end of the guide wire 16 may include a clamping mechanism 18 configured to releasably engage a driver 26 of the mitral valve implant 12. Referring to FIGS. 2 and 3, a close up of the clamping mechanism 18 of FIG. 1 is shown in the open and closed positions, respectively. The clamping mechanism 18 may include a first and at least a second jaw 30, 32 pivotably disposed relative to each other, for example along a pivot point 34. The first and second jaws 30, 32 may form a clam shell arrangement that defines an internal cavity or region 36 between the jaws 30, 32 sized and shaped to receive the driver 26 of the implant 12 when in the closed position as shown in FIG. 3. Additionally, the clamping mechanism 18 may include at least one opening or aperture 37 when in the closed position configured to receive at least a portion of the implant 12, for example, the shaft 52. The opening 37 may be disposed through one or more of the jaws 30, 32.

According to one embodiment, the clamping mechanism 18 may include a lower jaw 32 fixedly coupled to the guide wire 16 and an upper jaw 30 pivotably coupled to the lower jaw 32 about a pivot point 34. The upper jaw 30 may include an opening 40 configured to receive at least a portion of the lower jaw 32 when the upper and lower jaws 30, 32 are in the closed position. While the clamping mechanism 18 is shown having two jaws 30, 32, the clamping mechanism 18 may include three of more jaws. Additionally, while the position of the lower jaw 30 is shown generally fixed relative to the guide wire 16, either or both of the jaws 30, 32 may be pivotably coupled relative to the guide wire 16.

As best seen in FIG. 2, one or more of the interiors of the jaws 30, 32 may include at least one chamfered region 42 which may be configured to engage a portion of the driver 26 to open the clamping mechanism 18 as will be explained further below. For example, the upper and lower jaws 30, 32 may each include one or more of the chamfered regions 42a, 42b disposed proximate a front or distal-most end of the jaws 30, 32. One or more of the chamfered regions 42a, 42b may be configured to cam open the jaws 30, 32.

Figure 4:
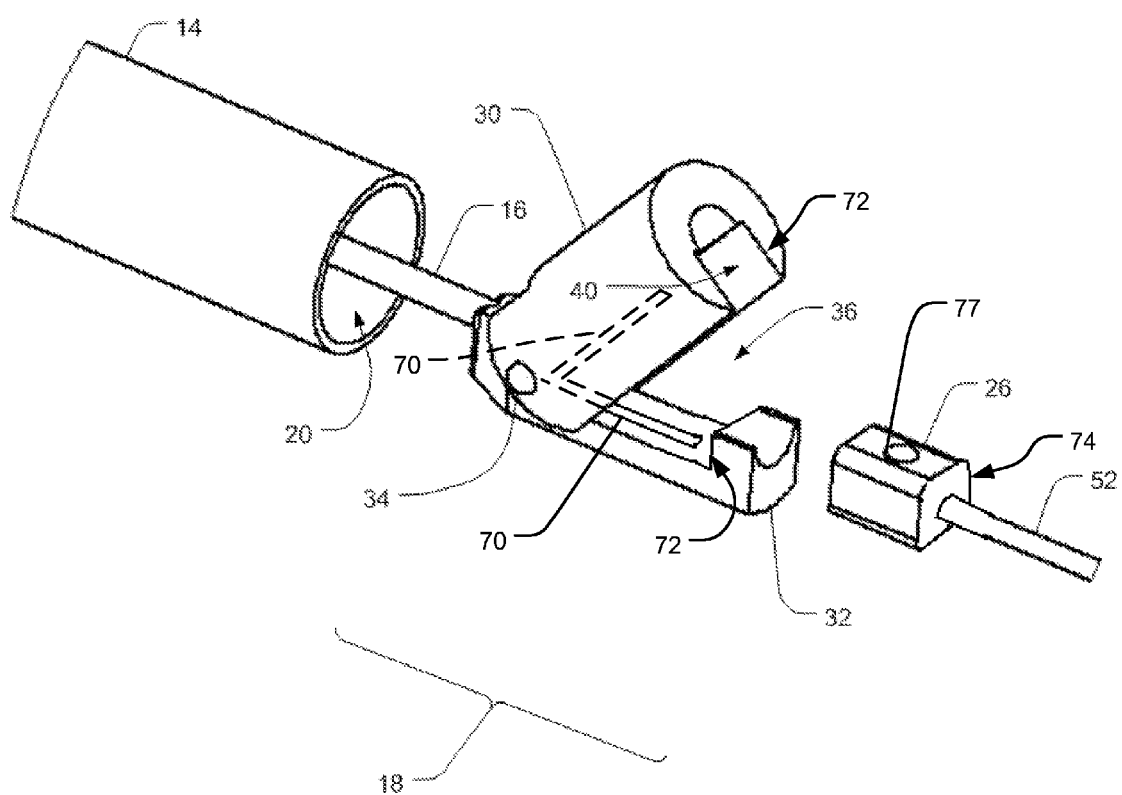
FIG. 4 depicts another embodiment of a clamping mechanism and driver in an open position.

Turning to FIG. 4, the clamping mechanism 18 may optionally include a biasing device 70 configured to urge the jaws 30, 32 towards the open position. The biasing device 70 may take the place of or be used in conjunction with the one or more of the chamfered regions 42a, 42b. According to one embodiment the biasing device 70 may include a spring or the like configured to urge the upper jaw 30 relative to the lower jaw 32. One or more of the jaws 30, 32 of the clamping mechanism 18 may optionally a shoulder region 72 configured to engage a portion of the driver 26. For example, a generally planar, upright or perpendicular shoulder region 72 may be configured to engage a generally planar, upright or perpendicular shoulder region 74 of the driver 26 when the clamping mechanism 18 is in the closed position preventing the driver 26 from being released from the clamping mechanism 18 as shown in FIG. 4. The shoulder region 72 may also be configured to engage one or more chamfered regions of the driver 26 as discussed below to facilitate opening of the clamping mechanism 18.

Figure 5:
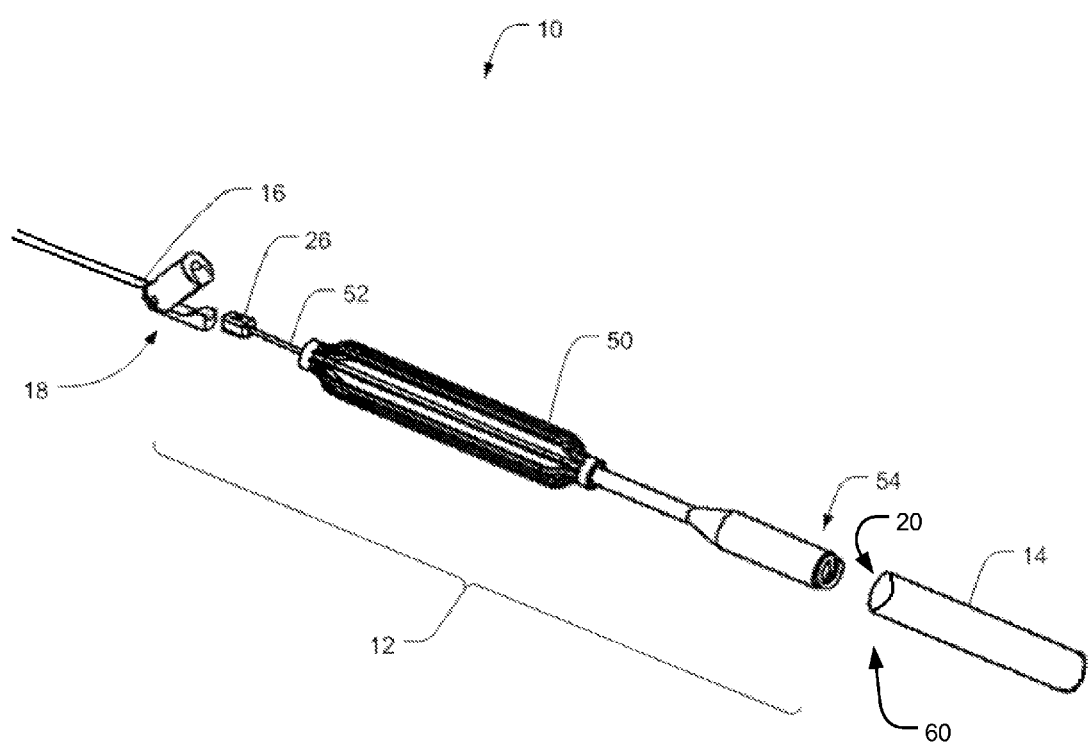
FIG. 5 depicts one embodiment of an implant and a guide wire including a clamping mechanism in the open position prior to loading into a catheter.

Turning now to FIGS. 1 and 5, the implant 12 may include any mitral valve implant such as, but not limited to, a mitral valve implant disclosed in U.S. patent application Ser. No. 11/258,828 filed Oct. 26, 2005 and entitled "Heart Valve Implant", which is fully incorporated herein by reference. For example, the mitral valve implant 12 may include a spacer or valve body portion 50 (for example, a resiliently deformable spacer configured to be received in the lumen 20 of the catheter 14) which may be coupled to a shaft 52. The shaft 52 may be coupled to at least one anchor portion 54 configured to couple, attach, and/or otherwise secure the mitral valve implant 12 to native coronary tissue. According to one embodiment, at least a portion of the anchor portion 54 may include a generally helical screw or the like configured to be at least partially screwed into the native coronary tissue.

In general, the mitral valve implant 12 may be delivered within the heart and anchored to the native coronary tissue such that at least a portion of the spacer 50 is disposed proximate a mitral valve and the mitral valve implant 12 may interact and/or cooperate with at least a portion of the native mitral valve to reduce and/or eliminate excessive regurgitation. For example, at least a portion of one or more cusps of the heart valve may interact with, engage, and/or seal against at least a portion of the heart valve implant 12 when the heart valve is in a closed condition. The interaction, engagement and/or sealing between at least a portion of at least one cusp and at least a portion of the heart valve implant 12 may reduce and/or eliminate regurgitation in a heart valve, for example, providing insufficient sealing, including only a single cusp, e.g., following removal of a diseased and/or damaged cusp, and/or having a ruptured cordae. A heart valve implant 12 consistent with the present disclosure may be used in connection with various additional and/or alternative defects and/or deficiencies.

The implant 12 may also include at least one driver 26 configured to releasably engage the clamping mechanism 18 of the guide wire 16. The driver 26 may be coupled to at least a portion of the shaft 52. For example, the driver 26 may be rigidly or fixedly coupled about the distal end of the shaft 52 generally opposite the anchoring portion 54. According to one embodiment, the driver 26, FIG. 2, may be fixedly coupled to the distal end of the shaft 52 using at least one set screw 77 or the like extending through an aperture of the driver 26 configured to engage a portion of the shaft 52. According to another embodiment, the driver 26 may be welded or integrally formed with the shaft 52.

The driver 26 may be sized and shaped to be received in the cavity 36 defined by the clamping mechanism 18 such that a portion of the shaft 52 may extend out from the cavity 36 through the opening 37 of the clamping mechanism 18 when in the closed position. According to one embodiment, the driver 26 may include a non-circular shape configured to engage the cavity 36 of the clamping mechanism 18 to substantially prevent rotation of the driver 26 (and therefore the mitral valve implant 12) relative to the guide wire 16 when in the closed position. As shown, the driver 26 may have a generally rectangular shape.

The driver 26 may also include one or more chamfered regions 44 configured to engage one or more of the jaws 30, 32 to cam open the clamping mechanism 18. According to one embodiment, the driver 26 may include a first a second chamfered region 44a, 44b disposed about the upper and lower end regions of the driver 26 proximate the attachment point and/or interface between the driver 26 and the shaft 52. The chambered regions 44 may generally match or correspond to one or more chamfered regions 42 of the jaws 30, 32 and may facilitate opening of the clamping mechanism 18.

Figure 6:
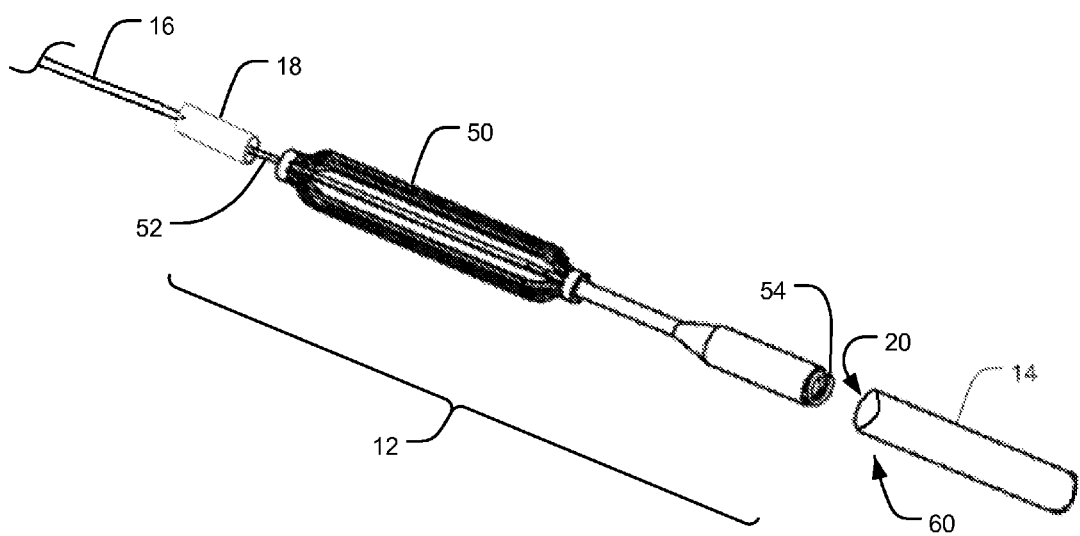
FIG. 6 depicts one embodiment of an implant disposed within a clamping mechanism prior to loading into a catheter.

In use, the jaws 30, 32 of the clamping mechanism 18 may be placed in the open position as generally shown in FIG. 5 and the driver 26 of the implant 12 may be loaded into the cavity 36 defined by the clamping mechanism 18. The jaws 30, 32 may then be closed around the driver 26 as generally shown in FIG. 6 such that the driver 26 is received within the cavity 36 of the clamping mechanism 18 and at least a portion of the shaft 52 of the implant 12 extends through the opening 37 of the clamping mechanism 18. The guide wire 16 and the implant 12 may then be loaded into a first end 60 of the lumen 20 of catheter 14, with the anchor portion 54 of the implant 12 being loaded first. Once the guide wire 16 and the implant 12 are loaded into the lumen 20, the internal diameter of the lumen 20 may be small enough such that the internal surface of the lumen 20 prevents the jaws 30, 32 of the clamping mechanism 18 from opening and releasing the driver 26, for example, between 5 French size and 50 French size. As a result, the clamping mechanism 18 may engage the driver 26 such that the driver 26 may be substantially coupled to the guide wire 16 while in the lumen 20. At least a portion of the implant 12 (for example, the spacer 50) may be deformable to facilitate loading of the implant 12 within the lumen 20.

Figure 7:
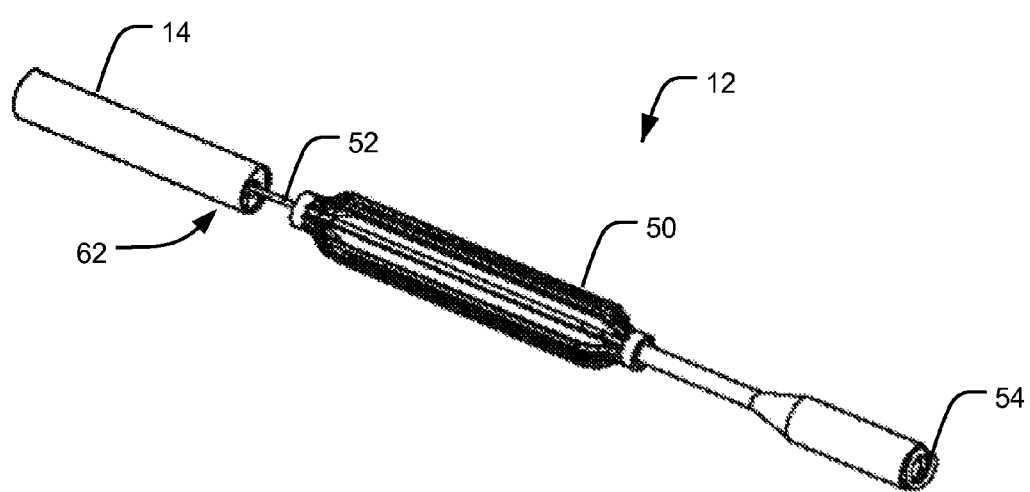
FIG. 7 depicts one embodiment of an implant and guide wire partially disposed within a catheter for securing the implant within the heart.

The guide wire 16 and implant 12 may then be conveyed through the lumen 20 of the catheter 14 (for example, by applying a force against the guide wire 16 to urge the guide wire 16 through the lumen 20) until at least a portion of the anchor portion 54 of the implant 12 extends outwardly beyond the second end 62 of the catheter 14 and the clamping mechanism 18 is at least partially received within the lumen 20 of the catheter 14 as generally shown in FIG. 7. Once the anchor portion 54 of the implant 12 is beyond the second end 62 of the catheter 14, the anchoring portion 54 of the implant 12 may be placed proximate the native coronary tissue and the guide wire 16 (and therefore the clamping mechanism 18) may be rotated within the catheter 14. According to one embodiment, the cavity 36 and the driver 26 may be configured such that the position of the driver 26 may be generally fixed within the cavity 36 of the clamping mechanism 18 as discussed above. As a result, rotation of the guide wire 14 may cause the implant 12 to rotate thereby causing the anchoring portion 54 to rotate and engage the native coronary tissue in the heart thus securing the implant 12 to the native coronary tissue in the heart.

Figure 8:
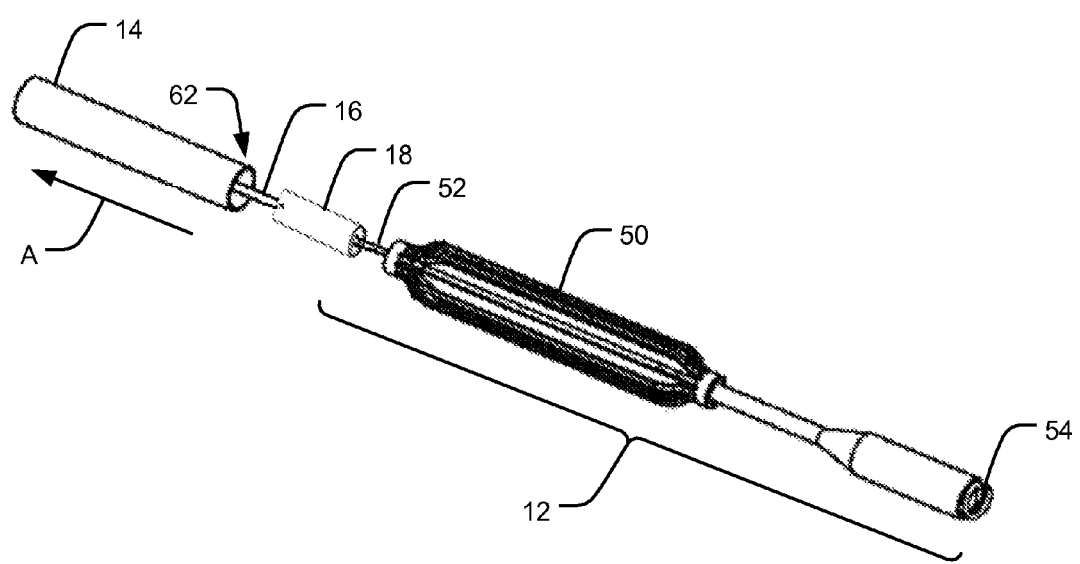
FIG. 8 depicts one embodiment of an implant and clamping mechanism disposed outside of the catheter.

Once the implant 12 is secured to the native coronary tissue in the heart, the catheter 14 may be pulled back generally away from the implant 12 in the direction of arrow A in FIG. 8 until the clamping mechanism 18 extends beyond the second end 62 of the catheter 14. Once the clamping mechanism 18 is exposed, the implant 12 may be released from the clamping mechanism 18. According to one embodiment, the implant 12 may be released from the clamping mechanism 18 by pulling the guide wire 16 generally away from the implant in the direction of arrow A. The chamfered regions 42 of the jaws 30, 32 may be configured to slide along the chamfered regions 44 of the driver 26 to cam open the jaws 30, 32 and release the driver 26 from the guide wire 16 as generally shown in FIG. 1. Alternatively (or in addition), the biasing device 70 of FIG. 4 may urge jaws 30, 32 open thereby releasing the implant 12 from the clamping mechanism 18 once the clamping mechanism 18 is outside of the catheter 14. In any event, once the implant 12 is released from the clamping mechanism 18, the guide wire 16 and clamping mechanism 18 may then be retracted back into the lumen 20 of the catheter 14 and the catheter 14 may be removed from the patient.

To recapture the implant 12, the catheter 14 may be placed proximate the implant 12. The guide wire 16 may be loaded into the catheter 13 and urged through the lumen 20 until the clamping mechanism 18 extends outwardly from the second end 62 of the catheter 14. With the clamping mechanism 18 in the open position as generally shown in FIG. 1, the jaws 30, 32 may be placed over the driver 26 and the catheter 14 may be slide over the clamping mechanism 18 causing the jaws 30, 32 to engage the driver 26 as generally shown in FIG. 7. The anchor portion 54 of the implant 12 may then be unscrewed by rotating the guide wire 14 and clamping mechanism 18. The implant 12 may then be repositioned within the heart or retracted into the catheter 14 by pulling the guide wire 16 in the direction of arrow A.

The implant 12 herein has been disclosed above in the context of a mitral valve implant. An implant 12 consistent with the present disclosure may also suitably be employed in other applications, e.g., as an implant associated with one of the other valves of the heart, etc. The present disclosure should not, therefore, be construed as being limited to use for reducing and/or preventing regurgitation of the mitral valve.

According to one aspect, the present disclosure features an implant delivery system comprising a catheter including at least one lumen, a guide wire configured to be received in the lumen, and an implant. The guide wire may comprise a clamping mechanism disposed about a distal end of the guide wire. The implant may be configured to be received in the lumen and may comprise a driver configured to be releasably received in the clamping mechanism of the guide wire.

According to another aspect, the present disclosure features a heart valve implant comprising a shaft, a spacer, at least one anchor coupled to a first end region of the shaft, and a driver. The spacer may be coupled to the shaft and may be configured to interact with at least a portion of at least one cusp of a heart valve to at least partially restrict a flow of blood through the heart valve in a closed position. The driver may be coupled to a second end region of the shaft generally opposite the first end region.

According to yet another aspect, the present disclosure features an implant delivery system for delivering an implant. The implant delivery system may comprise a catheter including at least one lumen and a guide wire configured to be received in the lumen. The guide wire may comprise a clamping mechanism disposed about a distal end of the guide wire. The clamping mechanism may also include a first and at least a second jaw wherein at least one of the jaws is configured to pivot between a closed position wherein the jaws define at least one internal cavity between the jaws configured to receive at least a portion of the implant and an open position configured to release the implant.

According to yet a further embodiment, the present disclosure features a method of delivering an implant within a heart using a guide wire. The implant may comprise a driver and the guide wire may comprise a clamping mechanism including a first and at least a second jaw. The method may comprise percutaneously delivering a catheter proximate the heart. The driver of the implant may be received within a cavity defined by the jaws of the clamping mechanism. The guide wire with the implant disposed within the cavity may be loaded into the catheter and conveyed through the catheter until an anchor portion of the implant extends outwardly beyond a distal end of the catheter and the clamping mechanism is still received within the catheter. The anchor portion of said implant may be secured within said heart. The guide wire may be conveyed through the catheter until the clamping mechanism and the implant are disposed outside of the catheter and the driver may be released from the clamping mechanism.

As mentioned above, the present disclosure is not intended to be limited to a system or method which must satisfy one or more of any stated or implied object or feature of the present disclosure and should not be limited to the preferred, exemplary, or primary embodiment(s) described herein. The foregoing description of a preferred embodiment of the present disclosure has been presented for purposes of illustration and description. It is not intended to be exhaustive or to limit the present disclosure to the precise form disclosed. Obvious modifications or variations are possible in light of the above teachings. The embodiment was chosen and described to provide the best illustration of the principles of the present disclosure and its practical application to thereby enable one of ordinary skill in the art to utilize the present disclosure in various embodiments and with various modifications as is suited to the particular use contemplated. All such modifications and variations are within the scope of the present disclosure as determined by the claims when interpreted in accordance with breadth to which they are fairly, legally and equitably entitled.

What is claimed:

1. A heart valve implant comprising:
   a shaft;
   a spacer coupled to said shaft and configured to interact with at least a portion of at least one cusp of a heart valve to at least partially restrict a flow of blood through said heart valve in a closed position; and
   a driver coupled to said shaft;
   wherein said spacer is deformable between an extended position in which said spacer is configured to interact with at least said portion of said at least one cusp of said heart valve to at least partially restrict said flow of blood through said heart valve in said closed position and a deformed position in which said spacer is configured to be received in a lumen of a delivery catheter.

2. The heart valve implant of claim 1, wherein said shaft extends from a first end region to a second end region.

3. The heart valve implant of claim 2, wherein said driver is coupled to the second end region of said shaft.

4. The heart valve implant of claim 2, further comprising at least one anchor coupled to the first end region of said shaft.

5. The heart valve implant of claim 4, wherein at least a portion of said at least one anchor is configured to at least partially engage with native coronary tissue of said heart.

6. The heart valve implant of claim 5, wherein said at least one anchor comprises a generally helical screw.

7. The heart valve implant of claim 1, wherein said driver comprises a generally perpendicular shoulder region.

8. The heart valve implant of claim 1, wherein said driver comprises an upper end region and a lower end region.

9. The heart valve implant of claim 8, wherein the upper end region and the lower end region comprise at least one chamfered region.

10. The heart valve implant of claim 9, wherein said driver is configured to be received in a cavity defined by a clamping mechanism and wherein said at least one chamfered region is configured to cam open said clamping mechanism.

11. The heart valve implant of claim 1, wherein said driver comprises at least one set screw extending through an aperture of said driver configured to fixedly couple said driver to said second end region of said shaft.

12. The heart valve implant of claim 1, wherein said driver is welded with the second end region of said shaft.

13. A heart valve implant comprising:
    a shaft having a first end region and a second end region;
    a spacer coupled to said shaft and configured to interact with at least a portion of at least one cusp of a heart valve to at least partially restrict a flow of blood through said heart valve in a closed position;
    an anchor coupled to a first end region of said shaft; and
    a driver coupled to a second end region of said shaft generally opposite said first end region; wherein said driver comprises an upper end region and a lower end region configured to be received in a cavity defined by a clamping mechanism;
    wherein said spacer is deformable between an extended position in which said spacer is configured to interact with at least said portion of said at least one cusp of said heart valve to at least partially restrict said flow of blood through said heart valve in said closed position and a deformed position in which said spacer is configured to be received in a lumen of a delivery catheter.

14. The heart valve implant of claim 13, wherein each of the upper end region and the lower end region comprises at least one chamfered region.

15. The heart valve implant of claim 14, wherein said driver is configured to be received in a cavity defined by a clamping mechanism and wherein said at least one chamfered region is configured to cam open said clamping mechanism.

16. The heart valve implant of claim 13, wherein said driver comprises at least one set screw extending through an aperture of said driver configured to fixedly couple said driver to said second end region of said shaft.

17. The heart valve implant of claim 13, wherein at least a portion of said at least one anchor is configured to at least partially engage with native coronary tissue of said heart.

18. The heart valve implant of claim 17, wherein said at least one anchor comprises a generally helical screw.

* * * * *